United States Patent

Niehren

(10) Patent No.: US 9,200,989 B2
(45) Date of Patent: Dec. 1, 2015

(54) METHOD AND DEVICE FOR THREE DIMENSIONAL MICRODISSECTION

(75) Inventor: Stefan Niehren, Altomuenster (DE)

(73) Assignee: MMI GmbH Molecular Machines & Industries, Eching bei Muenchen (DE)

( * ) Notice: Subject to any disclaimer, the term of this patent is extended or adjusted under 35 U.S.C. 154(b) by 739 days.

(21) Appl. No.: 12/256,341

(22) Filed: Oct. 22, 2008

(65) Prior Publication Data

US 2009/0140169 A1    Jun. 4, 2009

(30) Foreign Application Priority Data

Oct. 22, 2007   (EP) ..................... 07020582

(51) Int. Cl.
  *A01M 1/02*   (2006.01)
  *G01N 1/28*   (2006.01)
  G01N 1/06    (2006.01)
  G01N 1/42    (2006.01)

(52) U.S. Cl.
  CPC .............. *G01N 1/2813* (2013.01); *G01N 1/06* (2013.01); *G01N 1/42* (2013.01); *G01N 2001/2886* (2013.01)

(58) Field of Classification Search
  CPC ......... G01N 1/2813; G01N 1/06; G01N 1/42; G01N 2001/2886; G01N 21/4788; G21K 4/00; G21K 2004/06; C09K 11/7701; G01B 11/02; G01B 11/14; G01B 11/24; G03F 7/70625
  USPC .............. 435/173.9, 288.3, 6.1, 7.1, 460; 356/625; 250/483.1; 422/536; 382/133; 264/400; 977/889; 219/121.6–121.86; 607/80, 89, 92
  See application file for complete search history.

(56) References Cited

U.S. PATENT DOCUMENTS

| | | |
|---|---|---|
| 5,998,129 A | 12/1999 | Schutze et al. |
| 7,044,008 B1 | 5/2006 | Schuetze et al. |
| 2004/0045497 A1 | 3/2004 | Kriews et al. |
| 2005/0035305 A1 | 2/2005 | Kleinfeld et al. |
| 2006/0179992 A1 | 8/2006 | Kermani |
| 2007/0033681 A1 | 2/2007 | Lihl et al. |
| 2007/0160280 A1* | 7/2007 | Schutze et al. ............... 382/133 |

FOREIGN PATENT DOCUMENTS

| | | |
|---|---|---|
| DE | 10 2006 000 934 A1 | 7/2007 |
| WO | 97/29355 | 8/1997 |
| WO | 01/73398 A1 | 10/2001 |
| WO | 02/054057 A1 | 7/2002 |
| WO | 03/060477 A2 | 7/2003 |
| WO | 2004/061425 A1 | 7/2004 |
| WO | 2005/114135 A1 | 12/2005 |

* cited by examiner

*Primary Examiner* — Michael Hobbs
(74) *Attorney, Agent, or Firm* — Sughrue Mion, PLLC

(57) ABSTRACT

A method for three-dimensional microdissection for separating defined structures in the sub-millimeter range by cold laser ablation or multi-photon absorption, whereby exposure of the structures to be separated is performed using directional information in all spatial directions. Also, a 3D microdissection system for separating defined, three-dimensional structures from a sample, having: a control unit (5); an ablation chamber (1) with a sample holder, on which the sample to be processed is mounted and which is movable along a linear axis V and rotatable about a rotary axis R. The sample holder has positioning devices connected to the control unit. The positioning devices move the sample holder along another linear axis H and rotate it about rotary axis R, and a laser device (6) is introduced into the ablation chamber at least partially through a laser window (3) in the ablation chamber. The ablation chamber is connected to the control unit and has an adjustable optic, such that the laser beam is focused near the sample.

20 Claims, 1 Drawing Sheet

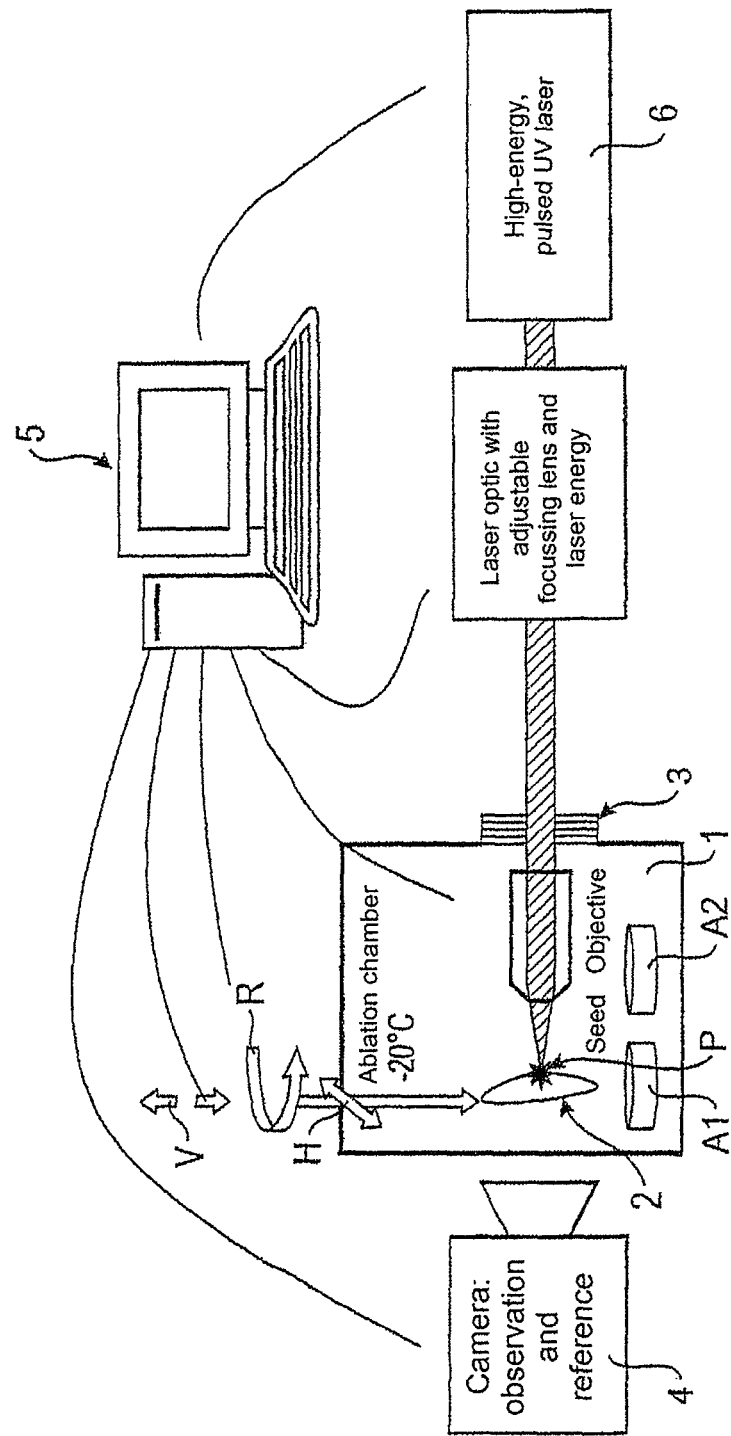

METHOD AND DEVICE FOR THREE DIMENSIONAL MICRODISSECTION

The following disclosure is based on European Patent Application No. 07 020 582.8, filed on Oct. 22, 2007, which is incorporated into this application by reference.

FIELD OF AND BACKGROUND

The present invention relates to a method for the separation of defined, three-dimensional structures especially from biological objects and a device for performing this method.

Microdissection permits the targeted isolation of mainly biological material from a sample. Typically in the prior art, mechanical or two-dimensional laser-based microdissection methods and devices are employed, using which it is possible to cut out and capture defined structures from the mainly biological samples.

A two-dimensional, laser-based microdissection method is described, for example, in DE 10 2006 000 934 A1. A biological preparation, a histological tissue section for example, is mounted therein on a carrier. Subsequently, selection of the preparation takes place by means of laser irradiation whereby a computer controls a motor-driven microscope stage on which the carrier is located. After cutting out an object, said object is accelerated by means of a laser shot and captured by a capturing means. Exposure of the structures to be separated is performed in this case by means of directional information in two spatial directions.

Further laser microdissection systems for objects which are disposed on a planar carrier are known from WO 97/29355 A and WO 01/73398 A.

The maximum cuttable layer thickness in laser-based microdissection methods is normally around 100 micrometers. Larger volumes with correspondingly greater layer thicknesses are not separable using known laser microdissection methods. The classic laser microdissection methods are all based on microscope assemblies in which the degrees of freedom of movement are restricted to the axes perpendicular to the optical axis. The classic processing method further requires sophisticated preparation of the sample as it is necessary first of all to create the sample layers to be processed in advance. Even preparation of the sample typically leads to changes and degeneration in the material to be examined in the last step of the process. In addition, it is not possible in the known laser-based microdissection methods to deep-freeze the sample during the entire treatment process. The microscope assembly of the classic systems dictates the use of a joint optical component, the objective, both for focussing the laser and also for imaging. A combination such as this dictates compromises both between the objective's imaging character in the visible light wave length range and also in transmission of the laser and the quality of laser focussing.

Thicker samples are also usable with the aid of mechanical methods. Nevertheless, it is difficult to cut deep-frozen materials mechanically. Furthermore, it is difficult to achieve a desirable accuracy for microscopic applications using mechanical methods.

Both the mechanical method and also classic laser microdissection are very time-consuming and thus the quantity of samples that can be produced is extremely limited. Many analysis methods of both proteomics and also of genomics are not suitable for such small sample quantities.

To analyse seed in early stages of growth, it is necessary to remove undisturbed and non-degraded cell material from a seed as it is only possible to generate usable analyses from undisturbed materials. Similar requirements for analysis also apply to the separation of biopsy materials. Thus, there is a need for microdissection methods and devices which can be used to isolate or separate non-degraded structures in a sample.

OBJECTS AND SUMMARY

One object of the present invention is thus to provide a method for the separation of defined, three-dimensional non-degraded or slightly degraded structures from a sample. Another is to provide a device for performing this method.

Accordingly, a method for three-dimensional microdissection for the separation of defined, three-dimensional structures from a sample is performed in the submillimeter range by means of cold laser ablation or by means of multi-photon absorption whereby exposure of the structures to be separated is carried out using directional information in all spatial directions. In this case, the submillimeter range includes the characteristic lengths of the structures to be separated up to one millimeter or a volume of the structures to be separated up to approximately 1 $mm^3$. Cold laser ablation is understood to be the removal of material by irradiation with short-wave laser light such that the sample is not heated up by photon absorption. That is to say, the laser light does not excite the molecular rotation and vibration bands. As an alternative to cold laser ablation, material processing may be based on multi-photon absorption processes. A very high photon density is generated in multi-photon absorption processes. As a result, the simultaneous absorption of a plurality of photons by the material becomes probable and the sum of the energies of the individual photons is thus incorporated in the material. For the most part, highly focussed lasers with extremely short laser pulses in the picosecond or femtosecond range are used to generate the high photon density. The sample preferably consists of a biological material. The laser preferably emits pulses with pulse times that are shorter than 5 ns.

The present invention pursues a completely new approach to the execution of laser-based microdissection. It becomes possible to dissect material volumes due to dispensing with the preparation of material layers and due to the increase in the number of degrees of freedom of movement. A sufficient number of degrees of freedom of movement enables the user to determine very flexibly and freely the shape of the material volume to be removed. Since it is possible with this approach to continue to implement a closed refrigeration chain from sample preparation up to sample analysis, it will become possible to produce virtually undisturbed and non-degenerated samples with a sufficient volume of samples. The production of sufficient quantities of samples places high demands on processing speed. Decoupling of the laser focussing optic from the observation optic enables optimum utilisation of the laser power available.

Realisation of the invention described on the basis of cold laser ablation is boosted by the availability of new solid-state lasers with pulse energies in the region of 100 μJ and repetition rates of several hundred Hertz.

According to one formulation, a method for three-dimensional microdissection for the separation of defined, three-dimensional structures from a sample preferably includes the following:

a) provision of a three-dimensional solid model of at least the structures to be separated;
b) at least partial cutting out of the structures to be separated according to the three-dimensional solid model by means of a three-dimensional cold laser ablation method; the procedure by means of three-dimensional cold laser ablation opens up a new method of sample processing. The method also enables the implementation of a closed refrigeration chain such that the sample is permanently refrigerated or cooled during the processing treatment. The method according to the present invention promises non-damaging removal of the structures to be separated which are also referred to in the following as VOI (volume of interest). By using the method it is possible to remove thin layers of the sample around the VOI one after another. This achieves a reduction in the microstructural change due to laser irradiation. In addition, the method of the present invention promises a level of precision in respect of the volume removed that has not previously been possible. Precision in the range of 10 μm can be achieved using this method.

The provision of a three-dimensional solid model according to step a) is carried out preferably by means of an imaging process that can at least capture the structures to be separated in their three-dimensional structures. Imaging processes for three-dimensional structures have undergone remarkable advances in recent years. There are standardised processes and systems available which can thus be integrated effectively and economically into the present method.

The imaging process preferably includes one of the following processes: nuclear resonance tomography, computed tomography, ultrasound, 3D modelling from light-optical microscopic visualisation processes; the processes referred to above are particularly widespread and highly developed and are, therefore, especially suitable for use in the present invention.

The imaging preferably includes a resolution in the 10 micrometer range. Imaging processes of the current generation may achieve a resolution in this range and thus contribute towards fulfilling the demand for particularly high separation precision in the present method. Alternatively, solid models may also be generated or drawn directly by the user based on parameterisations.

Optical parameters are preferably used for calibration and/or referencing to enable the position and alignment of the three-dimensional solid model to be harmonised with that of the sample introduced into the 3D microdissection. Optical parameters may be structural features already present in the sample or may be applied or introduced artificially. Alignment of the sample which is as accurate as possible in relation to the solid model is helpful in order to be able to perform a fully automated separation procedure. Performing alignment by way of optical parameters is to be preferred as it is possible to perform software-assisted alignment using optical components that may already be present at least in part. Thus a particularly high level of alignment precision is achievable which contributes towards fulfilling the requirement for a particularly high level of separation precision in the present invention.

The method of the present invention preferably further includes step a1), which is to be performed prior to step b), namely preparation of the sample so that the volume to be separated may be removed from it whereby preparation of the sample includes one of the following processes: embedding of the sample in synthetic materials, embedding of the sample in long-chain organic substances such as wax or paraffin, saturation of the samples with plasticising liquids, deep-freezing of the sample. Such preparation of the sample contributes towards the prevention of microstructural changes in the three-dimensional cold laser ablation method such that non-degraded or at least slightly degraded may be separated.

Preparation of the sample preferably includes deep-freezing of the sample at temperatures below 4° C. Freezing of the sample represents a particularly easy, fast and cost-effective possibility of reducing microstructural changes during the processing treatment.

The three-dimensional cold laser ablation method according to step b) preferably includes the following additional steps:

b1) mounting of the sample on a sample head, which is movable along an axis V and rotatable about a rotary axis R, whereby the movement may be performed automatically by means of appropriate positioning devices, which are linked to a control unit;

b2) specification of a movement sequence for the sample holder for sequential processing of the sample and saving thereof in a memory unit of the control unit, b3) performance of the ablation method by working through the movement sequence, whereby the control unit actuates the positioning devices according to the movement sequence. Using the method it is possible to remove thin layers of the sample one after another in order to expose the VOI. This achieves a reduction in the microstructural change due to laser irradiation. In addition, the method of the present invention promises a level of precision in respect of the volume removed that has not previously been possible. This is assisted in particular by the fully automated separation process, by which the laser and sample head are actuated on the basis of calculated movement steps such that inaccuracies, which are particularly unavoidable due to manual cutting out of the VOI, may be lessened.

Alternatively, the relative movement between laser focus and sample may also be implemented by an arrangement in which the laser assembly is mounted on a robot system and can thus be moved with sufficient degrees of freedom, and on which the sample is firmly attached.

Alternatively, the required degrees of freedom may be distributed between a movement of the laser assembly and the movement of the sample.

Exposure of the structures to be separated is preferably performed by means of a laser device, which is at least partially introduced into an ablation chamber in which exposure of the structures to be separated takes place. Lasers have recently gained in importance as cutting tools as they enable a particularly high level of cutting accuracy. Cuts may be performed precisely in a manner such that surrounding structures are unaffected or only slightly affected. Thus it is possible to separate non-degraded or at least slightly degraded structures with a high level of precision.

Step b) is preferably performed on an at least partially frozen sample. The present method enables separation on a deep-frozen sample, which contributes significantly towards the prevention of microstructural changes.

Furthermore, the method may be characterised in that one spatial dimension of the sample is at least one order of magnitude smaller than the other two.

The method according to the present invention preferably includes the step of monitoring the ablation process by using a camera assembly. Monitoring by means of a camera system, which is easy to install and cost-effective, lends itself to ensuring a desired standard of quality.

The camera assembly is preferably linked to the control unit, which by means of image processing methods and the characteristic optical parameters is used to calibrate and/or reference the absolute orientation of the sample, whereby the method includes the additional step, which is to be performed between step b1) and b3), of calibrating the sample with the three-dimensional solid model. In addition to monitoring the process, the camera assembly may also be used in a suitable manner for aligning the sample. Consequently, it is possible due to the dual function to save on costs and space.

Alternatively, the imaging system may be based on commercially available microscopes to which the camera may be connected.

The method of the present invention preferably includes step c), which is to be performed during and/or after step b), of cutting and removing of the separated structures whereby the step includes at least one of the following methods: collection of the falling separated structures in capture receptacles, firing off of partially separated structures by means of a laser shot, removal by adhesion, removal by suction, removal by rinsing, removal by ultrasound, removal by electrostatics; the methods referred to above are particularly suited to the removal and, if necessary, final cutting of the VOI as they can be performed easily and cost-effectively.

According to another formulation, the present invention provides a 3D microdissection system for the separation of defined, three-dimensional structures from a sample which includes:
  a control unit;
  an ablation chamber with a sample holder provided therein, on which the sample to be processed is to be mounted and which is movable along an axis V and rotatable about a rotary axis R, whereby the sample holder is provided with positioning devices that are connected to the control unit, which can cause the positioning devices to move the sample holder along axis V and rotate it about rotary axis R, and
  a laser device, which is introduced into the ablation chamber at least partially through a laser window that is provided in the ablation chamber, said laser device being connected to the control unit and having an adjustable optic which can be adjusted by means of the control unit such that the laser beam is focussed in the region of the sample or such that the sample can be moved into the laser focus along the optical axis by an additional positioning element. It is possible to carry out the above method with its advantages and benefits referred to above with the help of such a microdissection system.

In addition, the sample holder can preferably by moved along a third axis H by means of a positioning element, whereby the control unit is connected to this positioning device and can cause the positioning device to move the sample holder along axis H. It is necessary for the laser to be focussed accurately on the area to be cut. The provision of a further degree of freedom, which makes precise alignment of the sample easier, helps to bring the area of the sample that is to be cut into the focused area such that surrounding areas are not disturbed much. Thus it is possible to separate non-degraded or at least slightly degraded structures.

For the same reasons, the laser device preferably has a laser positioning device that is connected to the control unit whereby the tilt angle of the laser beam may be set by the control unit.

The sample holder is preferably a mechanical holder or a holder on which the sample is retained by means of embedding in a gel or similar.

Preferably, the ablation chamber has a refrigerating device, which can refrigerate the chamber such that the sample is frozen, preferably deep-frozen, or can be maintained in a frozen, preferably in a deep-frozen condition. Freezing of the sample represents a particularly easy, fast and cost-effective possibility of reducing microstructural changes during the processing treatment.

For this, the temperature in the ablation chamber is preferably lower than 4° C., typically approximately −18° C., since at these temperatures microstructural changes are significantly reduced with time.

Preferably, the optical axis of the laser stands perpendicular on rotary axis R, whereby rotary axis R and V coincide and stand perpendicular on axis H. The perpendicular or parallel arrangement of the axes can be executed with a high level of accuracy. In addition, such an arrangement can simplify calculation of the movement sequence.

Two capture containers A1 and A2 are preferably provided underneath the sample in the ablation chamber. Removal and separation of the VOIs by means of capture containers may be performed easily and cost-effectively.

According to yet another formulation, the present invention provides a 3D microdissection system for the separation of defined, three-dimensional structures from a sample which comprises:
  a control unit,
  a laser unit mounted on a robot system with sufficient degrees of freedom so that the laser focus can be aimed specifically at the sample,
  a miniature refrigeration chamber of laser-transparent material,
  a light-optical microscope for observation of the sample and the process sequence, as well as for accommodating the sample holder and the miniature refrigeration chamber.

BRIEF DESCRIPTION OF THE DRAWING

The FIGURE shows schematically a device for the separation of defined, three-dimensional structures from a sample according to an embodiment of the present invention.

DETAILED DESCRIPTION OF PREFERRED EMBODIMENTS

The FIGURE shows schematically a device for the separation of defined, three-dimensional structures from a sample according to an embodiment of the invention. The volume to be enucleated is also termed in the following as VOI (volume of interest).

In the present embodiment, a sample head with a sample 2 is located in an ablation chamber 1. Ablation chamber 1 comprises a housing in which the enucleation of defined, three-dimensional structures from the sample is performed. The sample head is disposed movably along a vertical axis V and a horizontal axis H and rotatably about a rotary axis R. Axes V and R may, as in the present embodiment, be identical. The movements of the sample head along axis V and H and about axis R are motorised by means of appropriate positioning devices which are not illustrated in the FIGURE. According to this embodiment, the sample head and the sample are movable by three degrees of freedom. The sample holder, for example, may be a mechanical holder or may be designed such that the sample is retained by means of embedding in a gel or similar. Ablation chamber 1 contains a refrigeration device, which is not illustrated in the FIGURE, such that the sample in the chamber may be deep-frozen or may be maintained in a deep-frozen state. The refrigeration device may comprise conventional refrigerators and sensors in order to adjust the temperature inside ablation chamber 1 to a desired value and to be able to keep it at this temperature.

Preparation of the sample is performed by means of a laser device 6, which, in addition to a high-energy, pulsed UV laser, comprises an adjustable laser optic with objective and is at least partially introduced into ablation chamber 1 through a laser window 3. In the present embodiment, an objective of laser device 6 is located inside ablation chamber 1. It is self-evident that, additionally or alternatively to the arrangement of the sample head that is moveable along three degrees of freedom, laser device 6 or a part of the laser device may also be arranged rotatably and/or movably. In particular, it is possible to provide a tilting function of the laser beam relative to the laser's optical axis in order to shift the laser's focal point P.

Control of the sample alignment along the degrees of freedom available is performed by a control unit 5, which in the present embodiment comprises a PC. This is connected to laser device 6 and the positioning devices. In addition, the PC may also be connected to the refrigerating device in order to monitor the temperature inside ablation chamber 1.

The preparation process is monitored using a camera assembly 4, which is likewise connected to the PC. Although camera assembly 4 in the FIGURE is indicated outside ablation chamber 1, it may also be provided inside ablation chamber 1. Camera assembly 4 serves not only for monitoring and quality assurance but is also used for calibrating and referencing characteristic optical parameters in order to harmonize the sample, as described further down, with a solid model.

A method for the separation of defined, three-dimensional structures, which uses the device referred to above, is described in the following.

First of all, a three-dimensional solid model of the sample or at least of the areas to be separated is created or obtained. For this purpose, models already available, for example also theoretical models, of the sample may be used. Typically, however, an imaging process, such as nuclear resonance tomography, computed tomography, ultrasound or light-optical microscopic processes, is used in this case. After taking a three-dimensional picture, it is saved in the control device in a computer model suitable for processing in a computer. The volumes to be enucleated are determined by means of a three-dimensional data field, whereby this data field is defined by the user by choosing the volume to be selected. Definition of the VOI may be performed both on the basis of prefabricated, generated solid models and also from direct 3D visualisations of the object to be processed. Alternatively, the VOI may also be calculated and generated from parameterisations or freehand drawings entered directly by the user.

Subsequently, the sample is introduced into an ablation chamber 1 preferably refrigerated to −18° C. and fixed using the sample holder. To enable the position of the visualised volume to be harmonised with the sample placed in the 3D microdissection system, it is necessary to introduce referencing methods such as calibration points or referencing by way of characteristic optical parameters. Referencing may be performed either by way of reference points applied artificially or also by way of characteristic structures of the object to be processed. One possible way of implementing optical visualisation consists of observing the sample with a macro objective and a digital camera which are contained in camera assembly 4. The objective and the camera may be provided directly in ablation chamber 1.

Referencing and calibration may be performed by means of camera assembly 4 and known image processing methods. Alignment of the sample with the solid model means defining a coordinate system of the data field relative to the mounted sample by way of a reference method.

There may also be computer-assisted calculation of a movement sequence, according to which control unit 5 actuates the positioning devices and the laser so that this laser cuts the areas to be separated. Thus a movement algorithm is calculated from the VOI which enables the VOI to be enucleated fully automatically in its entirety or in the form of fragments.

As the next step, a laser is introduced through laser window 3 and focussed on the sample by means of a lens. In this case, the laser's optical axis is essentially perpendicular to rotary axis R. Laser parameters such as laser power and focussing position are adjustable and may be adjusted in an appropriate manner by control unit 5.

The ablation process preferably starts at the bottom-most point of the sample and removes material in line with the movement sequence calculated during rotation of the sample about rotary axis R and movement of the sample along axes V and H. The material removed drops into a capture receptacle A1, which is provided underneath the sample in ablation chamber 1. Once a target volume has been enucleated, it is cut off from the remainder of the sample by laser beam and drops into a capture receptacle A2, which is likewise provided underneath the sample in ablation chamber 1. In this case, capture receptacles A1 and A2 can either be replaced or moved, or the sample head can be disposed directly over the relevant capture receptacle by means of the positioning devices.

The complete processing procedure may be documented, for example, by means of a digital camera. An additional image processing module may define the separated volumes and thus perform automatic quality control.

The invention claimed is:

1. A method for three-dimensional microdissection, to cut out a defined three-dimensional structure from a sample in the submillimeter range, comprising:
   providing a device for three-dimensional microdissection, the device comprising at least an ablation chamber and a laser device having an objective lens providing a laser focus, wherein the objective lens of the laser device is introduced into the ablation chamber to cut the sample,
   generating a three-dimensional volume model that defines the three-dimensional structure;
   cutting out the three-dimensional structure from the sample by performing at least one of cold laser ablation or multi-photon absorption based on the three-dimensional volume model that is defined by a three-dimensional data field comprising data representing all spatial directions,
   wherein the cutting out comprises relatively moving the sample with respect to the laser focus to remove layers of the sample in three dimensions by at least one of cold laser ablation or multi-photon absorption to thereby cut out the three-dimensional structure,
   wherein the three-dimensional structure remains undamaged when the cutting out is completed.

2. A method according to claim 1, wherein the sample consists of a biological material.

3. A method according to claim 1, wherein the laser emits pulses with pulse times smaller than 5 ns.

4. A method according to claim 1, wherein the generation of the three-dimensional volume model comprises an imaging process that captures at least the structures to be separated in three dimensions.

5. A method according to claim 4, wherein the imaging process includes at least one of the following processes: nuclear resonance tomography, computed tomography, ultrasound, and 3D modelling from light-optical microscopic visualisation processes.

6. A method according to claim 4, wherein the imaging has a resolution in the order of 10 micrometers.

7. A method according to claim 1, wherein the generation of the three-dimensional volume model is based on at least one of a user-defined parameterisation or a freehand drawing.

8. A method according to claim 1, wherein characteristic optical parameters are used for at least one of calibration and referencing to enable position and alignment of the three-dimensional volume model to be harmonised with position and alignment of the sample introduced into the three-dimensional microdissection.

9. A method according to claim 1, further comprising, prior to the exposure:
preparing the sample for removing the volume to be separated from the sample, whereby the preparation of the sample includes at least one of: embedding the sample in synthetic materials, embedding the sample in a long-chain organic substance, saturating the sample with a plasticizing liquid, and deep-freezing the sample.

10. A method according to claim 9, wherein the preparation of the sample includes deep-freezing of the sample to a temperature below 4° C.

11. A method according to claim 1, wherein the three-dimensional cold laser ablation process comprises:
mounting the sample on a sample head, which is movable along a first axis and rotatable about a rotary axis, whereby the movement is performed automatically by positioning devices, which are linked to a control unit;
defining a movement sequence for the sample head for sequential processing of the sample and saving the movement sequence in a memory unit of the control unit,
performing the ablation by executing the movement sequence, whereby the control unit actuates the positioning devices according to the movement sequence.

12. A method according to claim 1, wherein the exposure of the structures is performed with a laser device, which is at least partially introduced into an ablation chamber in which the exposure takes place.

13. A method according to claim 1, wherein the exposure is performed on an at least partially frozen sample.

14. A method according to claim 1, wherein one spatial dimension of the sample is at least one order of magnitude smaller than the other two dimensions of the sample.

15. A method according to claim 1, further comprising: monitoring the ablation process using a camera assembly.

16. A method according to claim 15, wherein the camera assembly is linked to the control unit, and further comprising:
at least one of calibrating and referencing an absolute orientation of the sample utilizing predetermined image processing methods and characteristic optical parameters, and
calibrating the sample with the three-dimensional solid model.

17. A method according to claim 1, further comprising:
cutting and removing the separated structures, the cutting and removing including at least one of: collecting the separated structures in capture receptacles, firing off partially separated structures with a laser shot, removing the separated structures by at least one of adhesion, suction, rinsing, ultrasound, and electrostatics.

18. A method according to claim 1, wherein the laser is a UV laser.

19. A method according to claim 1, wherein the structure is selectively isolated from the sample without being destroyed.

20. A method according to claim 1, wherein the cutting out of the three-dimensional structure from the sample is by performing at least cold laser ablation with a laser device, and wherein the ablation chamber maintains the temperature of the sample by using a refrigeration device.

* * * * *